(12) United States Patent
Desai

(10) Patent No.: US 8,530,409 B1
(45) Date of Patent: Sep. 10, 2013

(54) STABLE PEXIGANAN FORMULATION

(75) Inventor: Nayan Desai, Santa Rosa, CA (US)

(73) Assignee: Dipexium Pharmaceuticals LLC, White Plains, NY (US)

( * ) Notice: Subject to any disclaimer, the term of this patent is extended or adjusted under 35 U.S.C. 154(b) by 0 days.

(21) Appl. No.: 13/494,295

(22) Filed: Jun. 12, 2012

(51) Int. Cl.
*A01N 37/18* (2006.01)

(52) U.S. Cl.
USPC ............ 514/2.3; 514/1.1; 514/21.4; 424/405; 530/300; 530/326

(58) Field of Classification Search
None
See application file for complete search history.

(56) References Cited

U.S. PATENT DOCUMENTS 4,169,703 A * 10/1979 Fakhouri ............................ 8/421
4,335,125 A * 6/1982 Heeres et al. ............ 514/254.07
5,854,246 A * 12/1998 Francois et al. ......... 514/254.07
5,912,231 A * 6/1999 Houghten et al. ............. 514/3.2

OTHER PUBLICATIONS

Wahlberg, J. E. and Nilsson, G.; "Skin irritancy from propylene glycol." Acta. Derm. Venereol. (Stockh) (1984) 64 p. 286-290.*
Smales, C. Mark and James, David C. "Therapeutic proteins." Humana press, 2005 ISBN 1-59259-922-2.*
Pongcharoenkiat, Nongnuch et al; "The effect of surface charage and partition coefficient on the chemical stability of solutes in O/W emulsions." J. Pharma. Sci. (2002) 91(2) p. 559-570.*
Mupirocin package insert, manufactured by Perrigo, New York Inc, Jan. 2009.*
Merrifield, "Solid Phase Peptide Synthesis. I. The Synthesis of a Tetrapeptide", Jul. 20, 1963, pp. 2149-2154 (six (6) sheets).

* cited by examiner

*Primary Examiner* — Cecilia J Tsang
*Assistant Examiner* — Fred Reynolds
(74) *Attorney, Agent, or Firm* — Crowell & Moring LLP

(57) ABSTRACT

The invention provides chemically and physically stable topical formulations of pexiganan, and methods of preparing the same.

7 Claims, No Drawings

STABLE PEXIGANAN FORMULATION

FIELD OF THE INVENTION

The invention provides topical formulations of pexiganan which remain chemically and physically stable despite long term storage, and methods of preparing the same.

BACKGROUND OF THE INVENTION

One of the most significant concerns with treatment of wounds is infection. Infected wounds delay the wound healing process and increase hospitalization time. Wound infections often lead to secondary infections, amputations, and even death. The prevalence of antibiotic-resistant bacteria is an especially serious problem for treating wound infection. In fact, through extensive long-term use, most antibiotics actually generate resistant bacteria.

One type of wound prone to infection are those associated with diabetes, including diabetic foot ulcers, the chronic wounds which often develop in diabetic patients. Wounds resulting from diabetic complications are prevalent. Diabetes can involve peripheral neuropathy, and increase the likelihood that infected wounds will not be treatable with systemic antibiotics. It may take several months for an ulcer to heal, placing the patient at risk of re-infection and new infections, including risk of bone infection (osteomyelitis) and/or progressive gangrene. Diabetes, generally, and diabetic foot infection, specifically, are the top causes of non-traumatic leg amputations in the developed world, and foot ulcers are now the most frequent cause of diabetes-related hospitalizations. Thus, wound infection is a major burden to both the patient and the healthcare system.

Systemic antibiotic treatments are often used to treat wound infection. However, systemic therapy often leads to several side effects, particularly in diabetic patients who generally have compromised kidney and liver function. In addition, systemic therapy often leads to the risk of insufficient tissue penetration, due to the impaired blood supply at the wound site. Most available systemic antibiotics generate resistant bacteria through extended use. Thus, an effective topical therapy is often preferred as a route of administration for the delivery of an antibiotic agent to a wound.

Pexiganan is a broad-spectrum antimicrobial peptide for topical administration. It has antimicrobial activity against Gram-positive and Gram-negative organisms that commonly infect skin and soft tissue. Pexiganan has the benefit of a low potential for induction of resistance and no cross-resistance with existing therapeutic antibiotics, as a consequence of its mechanism of action. However, a stable topical pexiganan composition has been very difficult to formulate and is not presently available.

Peptides are often challenging to formulate as they exhibit chemical instability, adopt multiple conformations, tend to self-associate and also exhibit complex physical instabilities, especially in topical form. Both chemical and physical stability are critical to an effective and commercial pharmaceutical formulation. An unstable formulation results in loss of potency and poor quality and patient compliance. Topical formulations, especially, must remain stable in the container while stored long term and then when applied to the skin. Thus, there remains a need for a dosage form for the topical administration of pexiganan, which provides effective treatment of wound infection, and which remains chemically and physically stable over a long storage term.

SUMMARY

The present invention overcomes the problems outlined above and advances the art by providing stable pexiganan formulations for topical administration. The formulations of the present invention have both increased chemical stability and physical stability over the long term.

As such, in one embodiment, the present invention provides a topical formulation comprising pexiganan or an acid addition salt thereof comprising a first hydrophilic surfactant having an HLB value between about 12 and about 17 and a second hydrophobic surfactant having an HLB value between about 3.5 and about 5.5, wherein the first hydrophilic and second hydrophobic surfactants comprise from about 1.5 to about 5.0% w/w of the formulation and the weight ratio of the first to second surfactants is such that the blended HLB is between 12.5 and about 14.5.

Preferably, the HLB value of the first hydrophilic surfactant is between about 13 and about 16, and more preferably, the HLB value of the first hydrophilic surfactant is 14.9. Preferably, the HLB value of the second hydrophobic surfactant is between about 3.5 and about 5.5, and more preferably, the HLB value of the second hydrophilic surfactant is 4.7.

Preferably, the first hydrophilic and second hydrophobic surfactants comprise from about 2% w/w to about 4.5 w/w of the formulation. More preferably, the first hydrophilic and second hydrophobic surfactants comprise about 3.5% w/w of the formulation.

Preferably, the blended HLB of the first hydrophilic and second hydrophobic surfactants is between about 12.5 and about 14.5. More preferably, the blended HLB of the first hydrophilic surfactants and second hydrophobic surfactants is 13.6. Also preferably, the blended HLB of the first hydrophobic surfactant and second hydrophobic surfactant is 14.4.

Preferably, the first hydrophilic surfactant is Tween 60 and the second hydrophobic surfactant is Span 60.

In another embodiment, the stable topical formulation may comprise 1.05 (% w/w) pexiganan acetate; 20.0 (% w/w) propylene glycol; 0.1 (% w/w) EDTA; 7.5 (% w/w) stearyl alcohol; 2.0 (% w/w) cetyl alcohol; 1.0 (% w/w) isopropyl myristate; 0.1 (% w/w) BHT; 0.43 (% w/w) Span 60; 3.07 (% w/w) Tween 60; 0.1 (% w/w) Tween 80 and (q.s.a.d.) sodium acetate buffer.

In another embodiment, the stable topical formulation may comprise 1.05 (% w/w) pexiganan acetate; 20.0 (% w/w) propylene glycol; 0.1 (% w/w) EDTA; 6.0 (% w/w) stearyl alcohol; 2.0 (% w/w) cetyl alcohol; 3.0 (% w/w) isopropyl myristate; 0.1 (% w/w) BHT; 0.17 (% w/w) Span 60; 3.33 (% w/w) Tween 60; 0.1 (% w/w) Tween 80 and (q.s.a.d.) sodium acetate buffer.

In a further embodiment, the present invention provides a method of treating a skin or wound infection comprising topically applying to a patient in need thereof at the site of infection an effective amount of the formulations of the present invention.

DETAILED DESCRIPTION

It has now been discovered that topical formulations can be prepared comprising pexiganan which are chemically and physically stable. Additional aspects of the present invention will become more apparent from the detailed description of the following embodiments.

For purposes of the present disclosure, the following terms have the following meanings:

The term "active ingredient" refers to an ingredient having a therapeutic or cosmetic activity.

The term "topical application" refers to an application to the skin, including skin wounds, hair, ears, mucous membranes, rectal application, nasal application, as well as dental application within the oral cavity.

The term "stable formulation" refers to any formulation having sufficient stability to have utility as a pharmaceutical agent. Preferably, the formulation has sufficient stability to allow storage at a convenient temperature, preferably between 10° C. and 30° C., for a reasonable period of time, preferably longer than one month, more preferably longer than three months, even more preferably longer than six months, and most preferably longer than one year. Preferably, the formulation remains stable over time at room temperature, i.e., 25° C.

The term "physical stability" means that the oil- and water emulsion holds together, exhibiting no separation between the oil and water phases, and no significant changes in the physical properties of the product.

The term "chemical stability" means that a desirable percentage of the therapeutic agent remains intact and the percentage of degradation products produced by chemical pathways such as oxidation or hydrolysis, are at an acceptable level. In particular, a formulation is generally considered chemically stable if the drug concentration degrades no more than 10% after long-term storage at the intended storage temperature of the product, i.e., it is important to keep the drug concentration about 90% for an effective product. The stability upon long-term storage may be shown, for example, using accelerated conditions, such as at least 6 at 40° C., as indicative of long-term storage at 25° C. Chemical degradation may be caused by several mechanisms, including hydrolysis, cleavage of disulfide bonds, pH, temperature, interaction between ingredients, oxidation, and/or light-catalyzed degradation.

The term "therapeutically effective amount" refers to the amount of polypeptide that is sufficient to show a meaningful benefit, e.g., healing of a wound, inhibition of proliferation, prevention or amelioration of bacterial contamination or infection, or an increase in rate of healing of a wound, inhibition of proliferation, prevention or amelioration of such contamination and infections. Preferably, the meaningful benefit is statistically significant as compared to a control. Contacting a subject with the pexiganan polypeptides can be done with an amount and for a time sufficient to reduce bacterial infection or presence.

The term "wound" as used herein refers to any type of injury in which the skin is torn, cut, punctured, or damaged in any way. The wound can be acute or chronic. Chronic wounds are those that are caused by a relatively slow process that leads to tissue damage. Chronic wounds include, for example, pressure, venous, and diabetic ulcers.

"Diabetic ulcers" and "diabetic foot infections", refers to types of non-healing wounds associated with people who have diabetes. Non-healing wounds of the diabetic foot are considered one of the most significant complications of diabetes, representing a major worldwide medical, social, and economic burden that greatly affects patient quality of life. Typically, an insufficiency in the circulation or other systemic support of the tissue causes it to fail and disintegrate leading to a chronic wound. Because non-healing wounds are associated with inadequate circulation, poorly functioning veins, poor constriction of the veins and capillaries of the outer extremities, and immobility, non-healing wounds occur most frequently in the elderly and in people with diabetes. Diabetics often suffer from nerve damage in their feet and legs, allowing small wounds or irritations to develop without awareness. Given the abnormalities of the microvasculature and other side effects of diabetes, these wounds take a long time to heal and require a specialized treatment approach for proper healing. In addition to the wound not healing, infection can then take hold of the site leading to a chronic abscess. Once the infection hits a critical point, the infection can spread locally or become systemic.

The term "subject" as used herein refers to a mammalian subject, preferably a human subject, more preferably a human subject having a chronic wound, e.g. a subject suffering from diabetes.

Magainins are naturally occurring cationic peptides found in animals. They have broad-spectrum antimicrobial activity through their interaction with anionic phospholipids of microbial cells, which result in disruption of the cell membranes. Pexiganan (also known as MSI 78) is a synthetic cationic peptide analog of magainin 2, a host defence peptide isolated from frog skin. The chemical composition of pexiganan is:

H-Gly-Ile-Gly-Lys-Phe-Leu-Lys-Lys-Ala-Lys-Lys-Phe-Gly-Lys-Ala-Phe-Val-Lys-Ile-Leu-Lys-Lys-NH$_2$ [SEQ ID NO:1]

The sequence of pexiganan consists of seven naturally occurring amino acids, six of which have the L-configuration, the seventh (glycine) being optically inactive. The peptide is isolated as its acetate salt form with some residual water as natural constituents of the drug substance.

The molecule is synthesized as a single diastereomer with all chiral centers of pre-defined stereochemistry. The empirical molecular formula of pexiganan is $C_{122}H_{210}N_{32}O_{22}$.

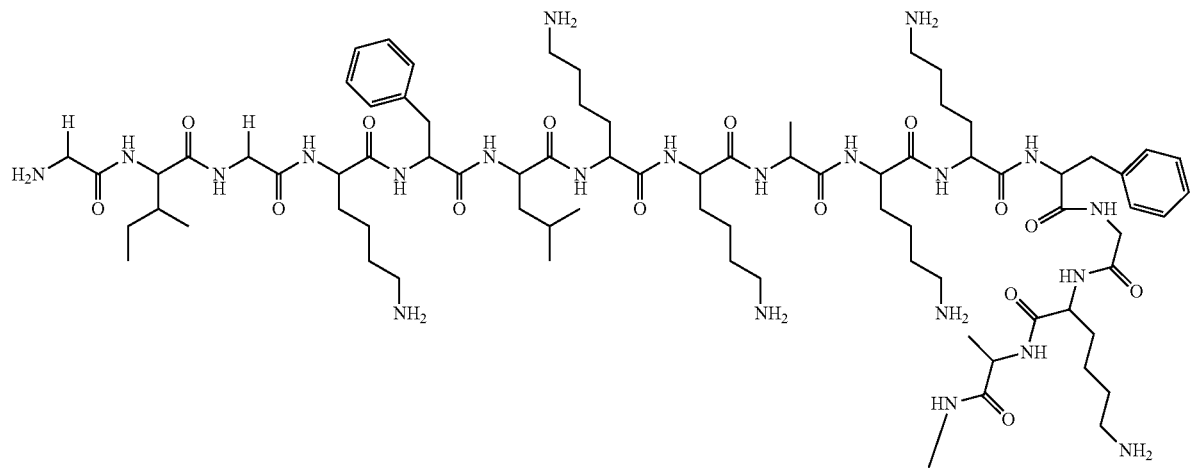

-continued

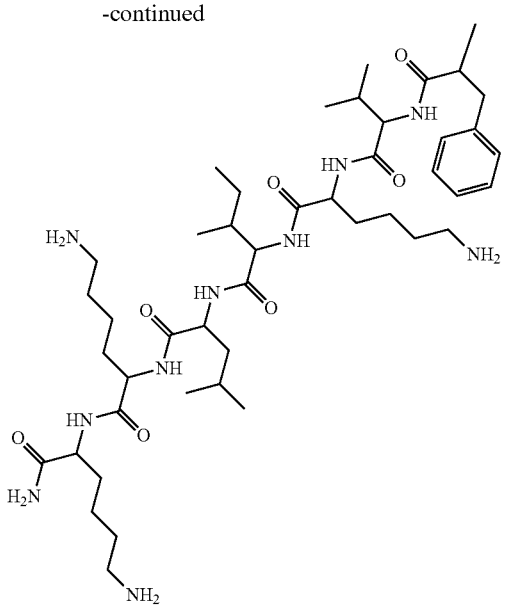

See U.S. Pat. No. 5,912,231, the entire content of which is hereby incorporated by reference.

Pexiganan has antimicrobial activity against Gram-positive (such as methycillin resistant staphylococcus aureus (MRSA)) and Gram-negative organisms that commonly infect skin and soft tissue. It has a low potential for induction of resistance and no cross-resistance with existing therapeutic antibiotics as a consequence of its mechanism of action. Pexiganan acts by causing lysis in the cells of microbes, thus acting as an effective inhibitor of proliferation of bacteria, including antimicrobial resistant bacteria. Pexiganan is effective in the topical treatment of wounds, where it inhibits proliferation of bacteria in the wound and treats bacterial infection. Preferably, the pexiganan is administered in an acid addition salt form, including pexiganan acetate.

Thus, pexiganan is an effective and preferred treatment for wound infections. However, a stable topical formulation suitable for pharmaceutical administration has not yet been achieved.

Chemical instability upon long-term storage is a common problem with peptide formulations. Over time, peptides may degrade via a number of mechanisms, including deamidation, oxidation, hydrolysis, disulfide interchange, and racemization. Unlike many therapeutic molecules, peptides do not have a globular structure that could sequester reactive groups, and thus the side chains of many peptides are exposed to reactive oxygen species. The high degree of flexibility of the peptide chain can lead to high rates of deamidation. The self-association behavior seen in peptides can lead to increased chemical instability. Highly self-associating peptides may even form micelles, affecting their ability to pass through membranes.

The nature of peptides also leads to physical instability in formulation. The ability of peptides to self-associate causes aggregates to form, eventually leading to large formations of aggregates.

The present invention provides a stable topical formulation able to overcome these problems associated with the long-term storage of peptide formulations. The formulations of the present invention comprise pexiganan and pharmaceutically acceptable excipients.

As the compositions described herein are administered topically, the compositions may be provided in a form suitable for topical administration, including, but not limited to creams, lotions, salves, gels, ointments or solutions, suspensions, emulsions, sprays or other forms suitable for topical administration. Preferably, the formulation is provided in the form of a cream or a gel.

Any suitable dosage of pexiganan can be administered via the methods of the present invention. Preferably, the pexiganan is in an acid addition salt form and preferably, the addition salt form is the acetate form. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. A preferred concentration of pexiganan acetate is 1-3% w/w of the formulation. More preferably, the concentration is 1.05% w/w.

The topical formulations described herein contain various excipients. The excipients chosen should generally not precipitate the pexiganan at the percentage used, should not cause any reactions harmful to the pexiganan, and should aid in the satisfactory solubilization and dispersion of the pexiganan. Excipients may include, without limitation, chelating agents, stiffening agents, antioxidants, emulsifiers, solvents, emollients, gelling agents, wetting agents, antimicrobial preservatives, anti-foaming agents, and pH adjusting agents.

The present formulations include emulsifiers. Emulsifiers may include, but are not limited to, Tween 60, Span 60, Tween 80, methyl glucose sesquistearate, PEG-20 methyl glucoside sesquistearate, Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 glyceryl monostearate, sucrose monostearate, sucrose polystearates, polyglyceryl 10 stearate, polyglcyeryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, steareth-2, PEG-5 soya sterol oil, PEG-10 soya sterol oil, diethanolamine cetyl phosphate, sorbitan monostearate, diethylenglycol monostearate, glyceryl monostearate, steareth-2 or -100, stearic acid, and mixtures thereof.

The formulation of the present invention comprises at least two emulsifiers. Preferably, the first emulsifier is a hydrophilic emulsifier. Preferably, this first hydrophilic emulsifier is Tween 60. Preferably, the second emulsifier is a hydrophobic emulsifier. Preferably, this second hydrophobic emulsifier is Span 60.

The hydrophile-lipophile balance (HLB) of the emulsifiers to oil phase also affects stability. The HLB is a measure of the degree to which a substance is hydrophilic or lipophilic, determined by calculating values for the different regions of the molecule. An HLB value of 0 corresponds to a completely hydrophobic molecule and a value of 20 corresponds to a completely hydrophilic molecule.

The ratio of the first emulsifier and the second emulsifier was unexpectedly found to be important to the chemical stability of the formulation. It was found that the ideal ratio of emulsifiers provided a significant improvement in long term chemical stability of the formulation at storage temperatures. While adjusting the ratio of the first and second emulsifiers, and thus adjusting the blended HLB of the two emulsifiers, was understood to affect physical stability, it was not expected to have any effect on chemical stability. However, by altering the ratio of the first hydrophilic emulsifier to the second hydrophobic emulsifier, the formulation was found to have a greatly enhanced chemical stability upon long term storage.

The first hydrophilic emulsifier has an HLB value of between about 12 and about 17. More preferably, the first hydrophilic emulsifier has an HLB value of between about 13 and about 16. For example, the HLB of the first hydrophilic emulsifier may be 14.9.

The second hydrophobic emulsifier has an HLB value of between about 3.5 and about 5.5. More preferably, the second hydrophobic emulsifier has an HLB value of between about 3.5 and about 5.5. For example, the HLB of the second hydrophobic emulsifier may be 4.7.

The first hydrophilic and second hydrophobic surfactants together may comprise from about 1.5 to about 5.0% w/w of the formulation. Preferably, the first hydrophilic and second hydrophobic surfactants comprise from about 2 to about 4.5% w/w of the formulation. More preferably, the first hydrophilic and second hydrophobic surfactants comprise about 3.5% w/w of the formulation. When the first a hydrophilic and the second emulsifier are present together, the blended HLB of the two emulsifiers may be measured. Blended HLB is calculated by taking the weighted average of the individual HLB values, as weighted by the percentage of the formulation comprised of the individual emulsifier. Preferably the blended HLB of the first hydrophobic emulsifier and second hydrophobic emulsifier is between about 12.5 and about 14.5. Also preferably, the blended HLB of the first hydrophobic surfactant and second hydrophobic surfactant is 14.4.

Further emulsifiers, such as a third or fourth, or more, emulsifiers, may be used in addition to the first emulsifier and second emulsifier.

The present formulations may include chelating agents. Preferred chelating agents include, but are not limited to for example, ethylenediaminetetraacetic acid (EDTA), disodium edetate and EDTA derivatives, citric acid, and mixtures thereof.

The present formulations may include stiffening agents, as used to increase the viscosity and/or increase consistency. Preferred stiffening agents may include, but are not limited to, stearyl alcohol, cetyl alcohol, waxes, ceteareth-20, ceteareth-30, cetearyl alcohol, ceteth 20, cetostearyl alcohol, cetyl alcohol, cetyl stearyl alcohol, and mixtures thereof.

The present formulations may include solvents. Preferred solvents include, but are not limited to, propylene glycol, water, isopropyl alcohol, liquid petrolatum, ether, petroleum ether, alcohols (e.g., ethanol and higher alcohols), silicones, aromatics (e.g., toluene), alkanes (e.g., pentane, hexane and heptane), ketones (e.g., acetone and methyl ethyl ketone), chlorinated hydrocarbons (e.g., chloroform, carbon tetrachloride, methylene chloride and ethylene dichloride), acetates (e.g., ethyl acetate), esters and oils (e.g., isopropyl myristate, diisopropyl adipate and mineral oil) and mixtures thereof. The solvent may also have antimicrobial properties.

The present formulations may include preservatives. Preferred preservatives may include, but are not limited to, phenoxyethanol, parabens (such as methylparaben and propylparaben), propylene glycols, sorbates, urea derivatives (such as diazolindinyl urea), and mixtures thereof.

The present formulations may include emollients. Preferred emollients include, but are not limited to caprylic/capric triglycerides, castor oil, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, silicone compounds, stearyl alcohol, urea and mixtures thereof.

The present formulations may include antioxidants. Preferred antioxidants include, but are not limited to, butylated hydroxytolunene (BHT), butylated hydroxyanisole (BHA), propyl gallate, coenzyme Q10, rosemary oil, green tea, lycopene, grape seed extract, pine bark extract, Vitamin C, natural beta carotene, synthetic beta carotene, gamma-oryzanol (esters of ferrulic acid), selenium, lutein, and mixtures thereof.

The present formulations may include buffering agents. Preferred buffering agents include, but are not limited to, acetate buffers such as sodium acetate, citrate buffers, phosphate buffers, lactic acid buffers, borate buffers, and mixtures thereof. The pH of the present formulations is preferably between 4.0 and 6.0. More preferably, the pH of the present formulation is 5.0.

By way of example, a formulation may comprise pexiganan acetate, propylene glycol, EDTA, stearyl alcohol, cetyl alcohol, isopropyl myristate, BHT, 0.43 (% w/w) Span 60, 3.07 (% w/w) Tween 60, Tween 80, and sodium acetate buffer. For example, a formulation may be:

| Ingredient | % w/w |
| --- | --- |
| Pexiganan Acetate | 1.05 |
| Propylene Glycol | 20.00 |
| EDTA | 0.10 |
| Stearyl Alcohol | 7.50 |
| Cetyl Alcohol | 2.00 |
| Isopropyl Myristate | 1.00 |
| BHT | 0.10 |
| Span 60 | 0.43 |
| Tween 60 | 3.07 |
| Tween 80 | 0.10 |
| Sodium Acetate Buffer (63.4 mM) | q.s.a.d. |

A further formulation may be:

| Ingredient | % w/w |
| --- | --- |
| Pexiganan Acetate | 1.05 |
| Propylene Glycol | 20.00 |
| EDTA | 0.10 |
| Stearyl Alcohol | 6.00 |
| Cetyl Alcohol | 2.00 |
| Isopropyl Myristate | 3.00 |
| BHT | 0.10 |
| Span 60 | 0.43 |
| Tween 60 | 3.07 |
| Tween 80 | 0.10 |
| Sodium Acetate Buffer (63.4 mM) | q.s.a.d. |

A further formulation may be:

| Ingredient | % w/w |
| --- | --- |
| Pexiganan Acetate | 1.05 |
| Propylene Glycol | 20.00 |
| EDTA | 0.10 |
| Stearyl Alcohol | 6.00 |
| Cetyl Alcohol | 2.00 |
| Isopropyl Myristate | 3.00 |
| BHT | 0.10 |
| Span 60 | 0.17 |
| Tween 60 | 3.33 |
| Tween 80 | 0.10 |
| Diluted Hydrochloric Acid | q.s. pH 5.0 |
| 10% Sodium Hydroxide | q.s. pH 5.0 |
| Sodium Acetate Buffer (26.54 mM) | q.s.a.d. |

A further formulation may be:

| Ingredient | % w/w |
| --- | --- |
| Pexiganan Acetate | 1.05 |
| Propylene Glycol | 20.00 |
| EDTA | 0.10 |
| Stearyl Alcohol | 7.50 |
| Cetyl Alcohol | 2.00 |
| Isopropyl Myristate | 1.00 |
| BHT | 0.10 |
| Span 60 | 0.43 |
| Tween 60 | 3.07 |
| Tween 80 | 0.10 |
| Propylparaben | 0.08 |
| Methylparaben | 0.03 |
| Diluted Hydrochloric Acid | q.s. pH 5.0 |
| 10% Sodium Hydroxide | q.s. pH 5.0 |
| Sodium Acetate Buffer (63.4 mM) | q.s.a.d. |

A further formulation may be:

| Ingredient | % w/w |
| --- | --- |
| Pexiganan Acetate | 1.05 |
| Propylene Glycol | 5.00 |
| EDTA | 0.10 |
| Stearyl Alcohol | 7.50 |
| Cetyl Alcohol | 2.00 |
| Isopropyl Myristate | 1.00 |
| BHT | 0.10 |
| Span 60 | 0.43 |
| Tween 60 | 3.07 |
| Tween 80 | 0.10 |
| Diluted Hydrochloric Acid | q.s. pH 5.0 |
| 10% Sodium Hydroxide | q.s. pH 5.0 |
| Sodium Acetate Buffer (63.4 mM) | q.s.a.d. |

A further formulation may be:

| Ingredient | % w/w |
| --- | --- |
| Pexiganan Acetate | 1.05 |
| Propylene Glycol | 10.00 |
| EDTA | 1.10 |
| Stearyl Alcohol | 6.00 |
| Cetyl Alcohol | 2.00 |
| Isopropyl Myristate | 3.00 |
| BHT | 0.10 |
| Span 60 | 0.17 |
| Tween 60 | 3.33 |
| Tween 80 | 0.10 |
| Diluted Hydrochloric Acid | q.s. pH 5.0 |
| 10% Sodium Hydroxide | q.s. pH 5.0 |
| Sodium Acetate Buffer (63.4 mM) | q.s.a.d. |

The methods of administering a topical formulation is known to one of skill in the art. The present invention provides a method of treating a skin or wound infection comprising topically applying to a patient in need thereof at the site of infection an effective amount of the formulations of the present invention.

Although the present invention has been described in detail with reference to specific examples, it is understood that various modifications can be made without departing from the spirit of the invention, and would be readily known to the skilled artisan.

EXAMPLES

The following formulations were tested in the examples set forth below:

| FORMULATION COMPOSITIONS | | | |
| --- | --- | --- | --- |
| Component (% w/w) | 3216-6 | 3216-10 | 3216-72 |
| Pexiganan Acetate | 1.05 | 1.05 | 1.05 |
| Propylene Glycol | 20.00 | 20.00 | 20.00 |
| EDTA | 0.10 | 0.10 | 0.10 |
| Stearyl Alcohol | 7.50 | 7.50 | 6.00 |
| Cety Alcohol | 2.00 | 2.00 | 2.00 |
| Isopropyl Myristate | 1.00 | 1.00 | 3.00 |
| BHT | 0.10 | 0.10 | 0.10 |
| Span 60 | 2.00 | 0.43 | 0.17 |
| Tween 60 | 1.50 | 3.07 | 3.33 |
| Tween 80 | 0.10 | 0.10 | 0.10 |
| Diluted Hydrochloric Acid | q.s pH 5.0 | q.s. pH 5.0 | q.s. pH 5.0 |
| 10% Sodium Hydroxide | q.s. pH 5.0 | q.s. pH 5.0 | q.s. pH 5.0 |
| Sodium Acetate Buffer | q.s.a.d. | q.s.a.d. | q.s.a.d. |

Formula 3216-6 has a blended HLB of 9.07 [9.1].
Formula 3216-10 has a blended HLB of 13.6.
Formula 3216-72 has a blended HLB of 14.4.

Example 1

Chemical Stability at 6 and 11 Months

Formulations 3216-6, 3216-10 and 3216-72 were tested for chemical stability. Stability was determined using HPLC testing. The chromatographic parameters used were as follows:

| | |
|---|---|
| Column: | Halo ® C18 2.7 μm, 4.6 × 150 mm |
| Injection Volume: | 20 μL |
| Column Temperature: | 70° C. |
| Flow Rate: | 1.4 mL/min |
| Detection: | 214 nm |
| Run Time: | 27 min |
| Mobile Phase A: | 5% Acetonitrile:5% Isopropanol:90% Water 0.1% Trifluoroacetic Acid |
| Mobile Phase B: | 70% Acetonitrile:20% Isopropanol:10% Water:0.1% Trifluoroacetic Acid |

The degradation of the drug was measured. Eleven month data and eighteen month chemical stability data are summarized below. The chemical stability of all three at 25° C., i.e., room temperature, is shown. As noted supra, testing 40° C. for a shorter time is indicative of stability at 25° C. for longer periods of time. Testing a formulation at 40° C. for six months is considered indicative of the stability of the same formulation at 25° C. for two years.

The results show that pexiganan is more chemically stable in the 3216-10 and 3216-72 formulations than in the 3216-6 formulation. As shown below, the drug concentration in 3216-6 dropped from 102.4% of label claim at t=0 (the initial point) to 87% at 6 months. It is highly desirable for a commercial formulation to maintain a drug concentration above the 90% mark to be considered stable. This is achieved by formulations 3216-10 and 3216-72.

Furthermore, at 40° C., more degradation of the drug substance was observed in 3216-6 than in 3216-10 and 3216-72. For example, at eleven months, the total degradants seen in formulation 3216-6 at 40° C. is almost twice the number seen in formulation 3216-10 at 40° C. This is a significant difference in chemical stability.

The results show below indicate that formulations 3216-10 and 3216-72 would be far more chemically stable at storage temperatures longer term than formulation 3216-6. The difference between formulations 3216-10 and 3216-72 versus 3216-06 lies in the ratio of emulsifiers.

Chemical Stability of Pexiganan Acetate 1% Creams: 11 months

| Batch # (Formula #) | Storage T (° C.) | Assay and degradants | 0 | 1 | 6 | 11 |
|---|---|---|---|---|---|---|
| 3216-6 | 25 | % LC | 102.4 | | 102.8 | 100.3 |
| | | Total degs | | | 1.55 | 2.06 |
| | 40 | % LC | 102.4 | 100.1 | 87.3 | 70.9 |
| | | Total degs | | | 10.39 | 20.47 |
| 3216-10 | 25 | % LC | 102.2 | | 102.8 | 101.1 |
| | | Total degs | | | 1.53 | 2.65 |
| | 40 | % LC | | 99.8 | 93.6 | 85.6 |
| | | Total degs | | | 5.76 | 11.62 |
| 3216-72 | 25 | % LC | 102.4 | | 102.1 | 100.4 |
| | | Total degs | | | 1.6 | 1.74 |
| | 40 | % LC | | 99.2 | 94.3 | 84.5 |
| | | Total degs | | | 6.2 | 12.43 |

For use as t = 0 value in lieu of actual initial values of degradation products

Stability Results for Pexiganan Acetate Cream 1.05% w/w at 6 months

| Formulation | Condition | % w/w | % LC | Pexiganan Acetate Retention Time | Unknown Retention Time | Unknown Relative Retention Time | % Area of Pexiganan Acetate[1] | Total Degradation Products, % Area |
|---|---|---|---|---|---|---|---|---|
| 3216-6 | 5° C. | 1.09 | 103.4 | 12.251 | 8.647 | 0.71 | 0.38 | 1.35 |
| | | | | | 9.840 | 0.80 | 0.74 | |
| | | | | | 11.538 | 0.94 | 0.24 | |
| 3216-6 | 25° C. | 1.08 | 102.8 | 12.261 | 8.642 | 0.70 | 0.38 | 1.55 |
| | | | | | 9.830 | 0.80 | 0.73 | |
| | | | | | 11.542 | 0.94 | 0.24 | |
| | | | | | 14.240 | 1.16 | 0.20 | |
| 3216-6 | 40° C. | 0.92 | 87.3 | 12.271 | 8.659 | 0.71 | 0.45 | 10.39 |
| | | | | | 9.509 | 0.77 | 0.35 | |
| | | | | | 9.839 | 0.80 | 0.76 | |
| | | | | | 10.605 | 0.86 | 1.42 | |
| | | | | | 10.853 | 0.88 | 0.24 | |
| | | | | | 11.027 | 0.90 | 0.95 | |
| | | | | | 11.166 | 0.91 | 0.23 | |
| | | | | | 11.231 | 0.92 | 0.36 | |
| | | | | | 11.546 | 0.94 | 0.39 | |
| | | | | | 11.798 | 0.96 | 0.26 | |
| | | | | | 12.646 | 1.03 | 0.48 | |
| | | | | | 14.185 | 1.16 | 0.26 | |
| | | | | | 14.866 | 1.21 | 2.61 | |
| | | | | | 17.318 | 1.41 | 1.63 | |
| 3216-10 | 5° C. | 1.09 | 103.6 | 12.255 | 8.657 | 0.71 | 0.38 | 1.58 |
| | | | | | 9.843 | 0.80 | 0.74 | |
| | | | | | 11.544 | 0.94 | 0.25 | |
| | | | | | 14.205 | 1.16 | 0.22 | |
| 3216-10 | 25° C. | 1.08 | 102.8 | 12.244 | 8.640 | 0.71 | 0.37 | 1.53 |
| | | | | | 9.833 | 0.80 | 0.74 | |
| | | | | | 11.536 | 0.94 | 0.22 | |
| | | | | | 14.172 | 1.16 | 0.20 | |

Stability Results for Pexiganan Acetate Cream 1.05% w/w at 6 months

| Formulation | Condition | % w/w | % LC | Pexiganan Acetate Retention Time | Unknown Retention Time | Unknown Relative Retention Time | % Area of Pexiganan Acetate[1] | Total Degradation Products, % Area |
|---|---|---|---|---|---|---|---|---|
| 3216-10 | 40° C. | 0.98 | 93.6 | 12.296 | 8.655 | 0.70 | 0.37 | 5.76 |
| | | | | | 9.848 | 0.80 | 0.79 | |
| | | | | | 10.616 | 0.86 | 0.49 | |
| | | | | | 11.035 | 0.90 | 0.84 | |
| | | | | | 11.179 | 0.91 | 0.21 | |
| | | | | | 11.242 | 0.91 | 0.26 | |
| | | | | | 11.558 | 0.94 | 0.33 | |
| | | | | | 11.818 | 0.96 | 0.35 | |
| | | | | | 12.689 | 1.03 | 0.30 | |
| | | | | | 13.977 | 1.14 | 0.20 | |
| | | | | | 14.254 | 1.16 | 0.36 | |
| | | | | | 14.947 | 1.22 | 0.80 | |
| | | | | | 17.447 | 1.42 | 0.45 | |
| 3216-72 | 5° C. | 1.09 | 103.6 | 12.273 | 8.663 | 0.71 | 0.36 | 2.03 |
| | | | | | 9.853 | 0.80 | 0.75 | |
| | | | | | 11.555 | 0.94 | 0.24 | |
| | | | | | 14.227 | 1.16 | 0.20 | |
| | | | | | 14.655 | 1.19 | 0.26 | |
| | | | | | 18.007 | 1.47 | 0.22 | |
| 3216-13(A) | 25° C. | 1.07 | 102.1 | 12.269 | 8.674 | 0.71 | 0.38 | 1.60 |
| | | | | | 9.854 | 0.80 | 0.77 | |
| | | | | | 11.550 | 0.94 | 0.22 | |
| | | | | | 14.241 | 1.16 | 0.23 | |
| 3216-13(A) | 40° C. | 0.99 | 94.3 | 12.280 | 8.661 | 0.71 | 0.42 | 6.20 |
| | | | | | 9.511 | 0.77 | 0.20 | |
| | | | | | 9.851 | 0.80 | 0.76 | |
| | | | | | 10.620 | 0.86 | 0.68 | |
| | | | | | 10.862 | 0.88 | 0.23 | |
| | | | | | 11.036 | 0.90 | 0.84 | |
| | | | | | 11.242 | 0.92 | 0.29 | |
| | | | | | 11.553 | 0.94 | 0.30 | |
| | | | | | 11.808 | 0.96 | 0.31 | |
| | | | | | 12.668 | 1.03 | 0.25 | |
| | | | | | 13.957 | 1.14 | 0.21 | |
| | | | | | 14.226 | 1.16 | 0.23 | |
| | | | | | 14.932 | 1.22 | 0.91 | |
| | | | | | 17.434 | 1.42 | 0.57 | |

[1]Peaks ≧0.2% of the drug substance area were reported by RRT and % area relative to Pexiganan Acetate peak.

Stability Results for Pexiganan Acetate Cream 1.05% w/w at 11 months

| Formulation | Condition | % w/w | % LC | Pexiganan Acetate Retention Time | Unknown Retention Time | Unknown Relative Retention Time | % Area of Pexiganan Acetate[1] | Total Degradation Products, % Area |
|---|---|---|---|---|---|---|---|---|
| 3216-6 | 25° C. | 1.05 | 100.3 | 13.155 | 8.956 | 0.68 | 0.36 | 2.06 |
| | | | | | 10.157 | 0.77 | 0.75 | |
| | | | | | 11.392 | 0.87 | 0.21 | |
| | | | | | 11.532 | 0.88 | 0.32 | |
| | | | | | 11.922 | 0.91 | 0.21 | |
| | | | | | 16.992 | 1.29 | 0.22 | |
| 3216-6 | 40° C. | 0.74 | 70.9 | 13.150 | 8.836 | 0.67 | 0.38 | 20.47 |
| | | | | | 8.963 | 0.68 | 0.63 | |
| | | | | | 9.879 | 0.75 | 0.75 | |
| | | | | | 10.148 | 0.77 | 1.09 | |
| | | | | | 10.533 | 0.80 | 0.30 | |
| | | | | | 10.965 | 0.83 | 5.58 | |
| | | | | | 11.240 | 0.85 | 0.91 | |
| | | | | | 11.382 | 0.87 | 1.63 | |
| | | | | | 11.570 | 0.88 | 2.01 | |
| | | | | | 11.916 | 0.91 | 0.24 | |
| | | | | | 12.163 | 0.92 | 0.94 | |
| | | | | | 14.478 | 1.10 | 0.23 | |
| | | | | | 15.129 | 1.15 | 0.21 | |
| | | | | | 15.689 | 1.19 | 0.55 | |
| | | | | | 17.036 | 1.30 | 5.01 | |

-continued

Stability Results for Pexiganan Acetate Cream 1.05% w/w at 11 months

| Formulation | Condition | % w/w | % LC | Pexiganan Acetate Retention Time | Unknown Retention Time | Unknown Relative Retention Time | % Area of Pexiganan Acetate[1] | Total Degradation Products, % Area |
|---|---|---|---|---|---|---|---|---|
| 3216-10 | 25° C. | 1.06 | 101.1 | 13.152 | 8.967 | 0.68 | 0.38 | 2.65 |
|  |  |  |  |  | 10.160 | 0.77 | 0.79 |  |
|  |  |  |  |  | 10.890 | 0.83 | 0.36 |  |
|  |  |  |  |  | 11.399 | 0.87 | 0.46 |  |
|  |  |  |  |  | 11.542 | 0.88 | 0.43 |  |
|  |  |  |  |  | 11.941 | 0.91 | 0.24 |  |
| 3216-10 | 40° C. | 0.90 | 85.6 | 13.174 | 8.852 | 0.67 | 0.24 | 11.62 |
|  |  |  |  |  | 8.980 | 0.68 | 0.48 |  |
|  |  |  |  |  | 9.918 | 0.75 | 0.49 |  |
|  |  |  |  |  | 10.175 | 0.77 | 0.98 |  |
|  |  |  |  |  | 10.609 | 0.81 | 0.28 |  |
|  |  |  |  |  | 10.875 | 0.83 | 0.28 |  |
|  |  |  |  |  | 10.993 | 0.83 | 1.78 |  |
|  |  |  |  |  | 11.258 | 0.85 | 0.69 |  |
|  |  |  |  |  | 11.400 | 0.87 | 1.59 |  |
|  |  |  |  |  | 11.586 | 0.88 | 1.65 |  |
|  |  |  |  |  | 11.936 | 0.91 | 0.39 |  |
|  |  |  |  |  | 12.303 | 0.93 | 0.67 |  |
|  |  |  |  |  | 17.067 | 1.30 | 2.11 |  |
| 3216-13 (A) | 25° C. | 1.05 | 100.4 | 13.072 | 8.967 | 0.69 | 0.38 | 1.74 |
|  |  |  |  |  | 10.171 | 0.78 | 0.78 |  |
|  |  |  |  |  | 11.403 | 0.87 | 0.33 |  |
|  |  |  |  |  | 17.011 | 1.30 | 0.24 |  |
| 3216-13 (A) | 40° C. | 0.89 | 84.5 | 13.125 | 8.820 | 0.67 | 0.29 | 12.43 |
|  |  |  |  |  | 8.956 | 0.68 | 0.49 |  |
|  |  |  |  |  | 9.898 | 0.75 | 0.58 |  |
|  |  |  |  |  | 10.165 | 0.77 | 1.01 |  |
|  |  |  |  |  | 10.569 | 0.81 | 0.36 |  |
|  |  |  |  |  | 10.865 | 0.83 | 0.49 |  |
|  |  |  |  |  | 10.987 | 0.84 | 2.32 |  |
|  |  |  |  |  | 11.246 | 0.86 | 0.79 |  |
|  |  |  |  |  | 11.395 | 0.87 | 1.24 |  |
|  |  |  |  |  | 11.579 | 0.88 | 1.58 |  |
|  |  |  |  |  | 11.916 | 0.91 | 0.38 |  |
|  |  |  |  |  | 12.278 | 0.94 | 0.55 |  |
|  |  |  |  |  | 17.059 | 1.30 | 2.35 |  |

[1]Peaks ≧0.2% of the drug substance area were reported by RRT and % area-relative to Pexiganan Acetate peak.

Example 2

Chemical Stability at 18 Months at 40° C.

The chemical stability of 3216-6, 3216-10, and 3216-72 is tested at 40° C. for 18 months, predictive of long term storage of the formulations at 25° C. Results are seen showing that the difference between the 3216-6 formulation compared to the 3216-10 and 3216-72 formulations at 40° C. shows a significant difference in the number of degradants. In other words, the difference in the number of degradants between the 3216-6 formulation versus the 3216-10 and -72 formulations at 18 months is greater than the difference seen between these same formulations at 11 months (shown above in Example 1).

Example 3

Physical Stability

Physical stability of the formulations was tested for appearance, pH (neat), viscosity at room temperature, and an assay of the active pharmaceutical ingredient was performed.

The samples were tested at 1, 2, and 3 months, at 5'C, 25° C. and 40° C. Testing at 40° C. provides a good indication of stability of a product that would be stored long term at 25° C. It is noted that testing at 40° C. for a short time such as six months, is considered indicative of stability at 25° C. (i.e., room temperature) for a longer period of time (twenty-four months).; i.e., it provides accelerated testing conditions.

The freeze/thaw cycle consisted of storage for three or four calendar days at −20° C., followed by storage for three or four calendar days at room temperature; a total of three cycles was performed.

Appearance, pH and viscosity were measured. Regarding appearance, a white or off-white smooth appearing cream, with no evident separation into separate phases, was preferred. Regarding pH, a suitable topical pH may include a pH between about 4.5 and about 8.

Regarding viscosity, the measurement of the cream at room temperature was performed. Viscosity values of 13 gram samples were measures on a rheometer equipped with a #29 Spindle, at 30 rpm, run at room temperature for 2 minutes. Ideal viscosities include a range of 5000-40000 centipoise, and are preferably between 10000 and 20000 centipose.

The results, showing these physical stability parameters, were as follows:

Pexiganan Acetate Cream 1.05%: Formula No.: 3216-6

| Storage Condition | Time Point (Month) | Appearance | pH (neat) | Viscosity[1] (cps) |
|---|---|---|---|---|
| N/A | T = 0 | Conforms | 5.02 | 10460 |
| F/T | 3 Cycles | Conforms | 5.01 | 9300 |

Pexiganan Acetate Cream 1.05%: Formula No.: 3216-6

| Storage Condition | Time Point (Month) | Appearance | pH (neat) | Viscosity[1] (cps) |
|---|---|---|---|---|
| 5° C. | 1 | Conforms | 5.06 | 7133 |
| | 2 | Conforms | 5.00 | 11360 |
| | 6 | Conforms | 5.06 | 6000 |
| 25° C. | 1 | Conforms | 5.06 | 13200 |
| | 2 | Conforms | 5.00 | 13900 |
| | 6 | Conforms | 5.04 | 12660 |
| | 11 | Conforms | NT | NT |
| | 18 | Conforms | 5.04 | 14660 |
| 40° C. | 1 | Conforms | 5.10 | 16660 |
| | 2 | Conforms | 5.01 | 16900 |
| | 6 | Conforms | 5.05 | 17760 |
| | 11 | Conforms | NT | NT |

[1] Viscosity parameters are as follows: Chamber 13R, Spindle 29, 30 rpm, 13 gram sample run at room temperature for 2 minutes.
Conforms = White to off-white smooth cream
NT = Not Tested (Not submitted for testing)

Pexiganan Acetate Cream 1.05%: Formula No.: 3216-10

| Storage Condition | Time Point (Month) | Appearance | pH (neat) | Viscosity[1] (cps) |
|---|---|---|---|---|
| N/A | T = 0 | Conforms | 4.82 | 17030 |
| F/T | 3 Cycles | Conforms | 4.88 | 10930 |
| 5° C. | 1 | Conforms | 4.89 | 18300 |
| | 2 | Conforms | 4.83 | 16360 |
| | 3 | NT | NT | NT |
| | 6 | Conforms | 4.76 | 9100 |
| 25° C. | 1 | Conforms | 4.89 | 12430 |
| | 2 | Conforms | 4.82 | 12100 |
| | 3 | NT | NT | NT |
| | 6 | Conforms | 4.76 | 10160 |
| | 11 | Conforms | NT | NT |
| | 18 | Conforms | 4.78 | 8266 |
| 40° C. | 1 | Conforms | 4.89 | 19700 |
| | 2 | Conforms | 4.83 | 21330 |
| | 3 | NT | NT | NT |
| | 6 | Conforms | 4.77 | 20200 |
| | 11 | Conforms | NT | NT |

[1] Viscosity parameters are as follows: Chamber 13R, Spindle 29, 30 rpm, 13 gram sample run at room temperature for 2 minutes.
Conforms = White to off-white smooth cream
NT = Not Tested (Not submitted for testing)

Pexiganan Acetate Cream 1.05%: Formula No.: 3216-72

| Storage Condition | Time Point (Month) | Appearance | pH (neat) | Viscosity[1] (cps) |
|---|---|---|---|---|
| N/A | T = 0 | Conforms | 4.99 | 19660 |
| F/T | 3 Cycles | Conforms | 5.09 | 11230 |
| 5° C. | 1 | Conforms | 5.04 | 15930 |
| | 2 | Conforms | 4.99 | 16160 |
| | 3 | NT | NT | NT |
| | 6 | Conforms | 4.93 | 10400 |
| 25° C. | 1 | Conforms | 5.06 | 14030 |
| | 2 | Conforms | 4.99 | 14400 |
| | 3 | NT | NT | NT |
| | 6 | Conforms | 4.93 | 12160 |
| | 11 | Conforms | NT | NT |
| 40° C. | 1 | Conforms | 5.06 | 18100 |
| | 2 | Conforms | 5.01 | 18860 |
| | 3 | NT | NT | NT |
| | 6 | Conforms | 4.95 | 20300 |
| | 11 | Conforms | NT | NT |

[1] Viscosity parameters are as follows: Chamber 13R, Spindle 29, 30 rpm, 13 gram sample run at room temperature for 2 minutes.
Conforms = White to off-white smooth cream
NT = Not Tested (Not submitted for testing)

Example 4

Stress Testing

Centrifugation stress testing was performed to help assess the likelihood of the product holding together over long term storage. The formulations were stress tested in a centrifuge, as shown below. Formulation 3216-10 was identical to the formulation 3216-6 in all aspects except for the ratio of two emulsifiers, Span 60 and Tween 60. In 3216-6, the % w/w ratio is 2:1.5, whereas in 3216-10 this ratio was changed to 0.43:3.07. The total amount of the two emulsifiers stayed the same at 3.5% w/w. However, the adjustment of the ratio of the two resulted in superior stability. Formulation 3216-10 was better able to maintain its physical integrity in the stress test as evidenced by the time required to show phase separation. In the centrifugation test at 25° C., while 3216-6 showed separation after 10 minutes at 5000 g, 3216-10 took 60 minutes under similar stress conditions to exhibit separation. In a similar test done at 40° C. (accelerated conditions), while 3216-6 separated after 60 minutes, no such separation was observed with 3216-10.

TABLE 3

Stress Testing of the Pexiganan Acetate Cream

| Formulation No. | Conditions | Initial pH | pH | Appearance | Viscosity, cps | Phase Separation Point in Centrifugation Testing[2] 25° C. | 40° C. |
|---|---|---|---|---|---|---|---|
| 3216-6 | 5° C. | 5.07 | 5.06 | Conforms | 6480 | Sign of separation @ 5000 g, 10 min | Sign of separation @ 5000 g, 60 min |
| | 25° C. | | 5.02 | Conforms | 10980 | | |
| | 40° C. | | 5.09 | Conforms | 10420 | | |
| | 50° C. | | 5.04 | Conforms | 12780 | | |
| | −20° C./40° C. | | 4.93 | Conforms | 10580 | | |
| 3216-10 | 5° C. | 5.08 | 5.11 | Conforms | 9880 | Sign of separation @ 5000 g, 60 min | No separation |
| | 25° C. | | 5.07 | Conforms | 17400 | | |
| | 40° C. | | 5.12 | Conforms | 17160 | | |
| | 50° C. | | 5.1 | Conforms | 17840 | | |
| | −20° C./40° C. Cycles | | 4.94 | Conforms | 16040 | | |

[1] Smooth white to off-white viscous cream

Example 5

Preparation of a Pexiganan Formulation

Step 1: The sodium acetate buffer was prepared by mixing the purified water, sodium acetate trihydrate and glacial acetic acid.

Step 2: In the main manufacturing vessel, propylene glycol, poylsorbate 60 and approximately 85% of the sodium acetate buffer were combined. The mixture was heated to 65-70° C. while propeller mixing. The temperature was maintained.

Step 3: In a second vessel, stearyl alcohol, cetyl alcohol, sorbitan monostearate, isopropyl myristate and BHT were combined, and heated to 65-70° C. while mixing to ensure that all solid materials were melted. The temperature was maintained.

Step 4: In a third vessel, the remainder of the sodium acetate buffer, polysorbate 80, disodium edetate and pexiganan acetate were combined, and heated to 35-45° C. with mixing until a clear solution was obtained. The temperature was maintained.

Step 5: With homogenization, the oil phase from step 3 was slowly added to the aqueous phase from step 2.

Step 6: Heating was discontinued. Homogenization was continued. The emulsion was cooled to 55° C. using an ice bath.

Step 7: Homogenization was stopped and the emulsion was removed from the ice bath.

Step 8: Propeller mixing was started. The drug phase from step 4 was added to the emulsion in step 7.

Step 9: With continuous propeller mixing, the batch was cooled to room temperature.

Step 10: The pH was recorded. If necessary, the pH was adjusted to 5.0±0.2 using 10% HCl or 10% NaOH. The product was mixed until smooth and homogeneous.

Example 6

Preparation and Purification of Pexiganan Acetate Active Ingredient

The active ingredient, pexiganan acetate, is provided as a lyophilized powder.

The peptide-resin precursor of pexiganan acetate was manufactured using the general procedure described in Merrifield (Solid Phase Peptide Synthesis. I. The Synthesis of a Tetrapeptide. *J. Am. Chem. Soc.* 1963 85 (14): 2149-2154), with minor modifications. The α-amino group of each amino acid was protected with the base-sensitive Fmoc group, while sidechain functional groups are protected with acid-labile groups. The synthesis was carried out using Fmoc-Rink Amide resin (substitution: approximately 0.7 meq/g) as the starting resin support for the manufacturing process. Standard Fmoc-chemistry was utilized for the peptide chain assembly, using the following general cycle:

removal of the N-terminal Fmoc-group of the starting resin or the last amino acid added using a 20% (v/v) solution of piperidine in DMF;
washing with DMF;
coupling of the next amino acid using DIC in the presence of HOBt; and
washing with DMF.

After removal of the Fmoc-group and washing with DMF, a small sample of the resin was removed and subjected to the ninhydrin in-process control test, a color test measuring residual resin-bound amine groups. The test was positive to confirm the presence of the free amine group.

This cycle was repeated with the appropriate amino acid derivatives, i.e., Fmoc-Lys(Boc)-OH, Fmoc-Lys(Boc)-OH, Fmoc-Leu-OH, Fmoc-Ile-OH, Fmoc-Lys(Boc)-OH, Fmoc-Val-OH, Fmoc-Phe-OH, Fmoc-Ala-OH, Fmoc-Lys(Boc)-OH, Fmoc-Gly-OH, Fmoc-Phe-OH, Fmoc-Lys(Boc)-OH, Fmoc-Lys(Boc)-OH, Fmoc-Ala-OH, Fmoc-Lys(Boc)-OH, Fmoc-Lys(Boc)-OH, Fmoc-Leu-OH, Fmoc-Phe-OH, Fmoc-Lys(Boc)-OH, Fmoc-Gly-OH, Fmoc-Ile-OH and Fmoc-Gly-OH. In-process monitoring, using the ninhydrin test, was performed at the end of each synthesis cycle as an evaluation of the coupling step. A negative test result indicated the absence of free amines (complete coupling). If the test was found to be positive, indicating unreacted amine (incomplete coupling), the coupling reaction may be prolonged, re-coupling of the protected amino acid derivative may be performed or acetylation (capping) may be performed, using acetic anhydride in the presence of DIEA.

The resin was washed with IPA and dried under a stream of nitrogen to give the protected peptide-resin precursor of pexiganan acetate. The product was detached from the resin and concomitantly deprotected by treatment of sublots of the peptide-resin precursor with a mixture of TFA and water (TFA:$H_2O$, approximately 95:5, v/v) for approximately two and a half hours at ambient temperature. The resin was then removed by filtration, washed with additional TFA, and the combined filtrates concentrated by rotary evaporation. The crude product was precipitated by adding the concentrated filtrates to MTBE, isolated by filtration, washed on the filter with MTBE, and dried to constant weight in a vacuum oven at ambient temperature.

The crude pexiganan from the previous step was purified by a two-step, preparative, RP-HPLC procedure, on $C_{18}$ reverse-phase silica, during which the purity of the fractions was assessed by analytical HPLC. In the first step of the process, sublots of the crude product were separately re-dissolved in dilute, aqueous acetic acid (approximately 10%, v/v), the solution filtered and applied to a preparative HPLC column that has been washed with methanol and equilibrated with 0.1 M aqueous triethylammonium phosphate, pH 2.3 (TEAP). The product was eluted using a gradient of acetonitrile in TEAP buffer, with monitoring by ultraviolet (UV) at 230 nm. The resulting fractions were analyzed by an in-process HPLC method and combined in such a way that the purity complies with the requirements for in-process controls. Fractions with purities of less than the in-process control criteria may be recycled through the above procedure or discarded.

In the second stage of the purification, the pool of semi-purified peptide from the first purification step was diluted and loaded onto a preparative column, which had been equilibrated with 0.1% aqueous TFA. The product was eluted using a gradient of acetonitrile in 0.1% aqueous TFA with monitoring by UV at 230 nm. The resulting fractions were analyzed by an in-process HPLC method and combined in such a way that the purity complied with the requirements for in-process controls. Fractions with purities of less than the in-process control criteria may be recycled through the above procedure or discarded.

The pooled fractions from the two step purification run were lyophilized separately to give sublots of the TFA salt of the purified product, which were stored under refrigeration prior to conversion to the acetate salt in the next step of the process.

The purified TFA salt of the product from the previous purification step was converted to the acetate salt by an ion exchange procedure using Dowex 1 X 2-100 resin. A solution of the pooled sublots in dilute aqueous acetic acid (approximately 10%, v/v) was passed through a column packed with an excess of Dowex 1 X 2-100 (acetate form), which was subsequently washed with additional aqueous acetic acid to recover the product completely.

The pooled eluents from the counter-ion exchange step were filtered and lyophilized to dryness to give the acetate salt of pexiganan.

The invention has been described by way of illustration, and not by limitation. It is to be understood that the particular embodiments depicted in the figures and the terminology which has been used has been intended in a nature of words of description rather than of limitation. It is to be further understood that any combination of the ingredients/therapeutic agents described in the foregoing paragraphs are deemed to be encompassed by the appended claims. It is to be further understood that all specific embodiments of the injection device are deemed to be encompassed by the appended claims. Many modifications and variations of the present invention are possible in light of the above teachings. It is therefore to be understood that the obvious modifications are deemed to be encompass within the appended claims.

What is claimed is:

1. A topical formulation comprising pexiganan or an acid addition salt thereof comprising a first hydrophilic surfactant having an HLB value between about 12 and about 17 and a second hydrophobic surfactant having an HLB value between about 3.5 and about 5.5, wherein the first hydrophilic and second hydrophobic surfactants comprise from about 1.5% w/w to about 5.0% w/w of the formulation and the weight ratio of the first to second surfactants is such that the blended HLB is between 12.5 and about 14.5, wherein the first hydrophilic surfactant is Tween 60 and the second hydrophobic surfactant is Span 60.

2. The topical formulation of claim 1, wherein the first hydrophilic and second hydrophobic surfactants comprise from about 2% w/w to about 4.5% w/w of the formulation.

3. The topical formulation of claim 1, wherein the first hydrophilic and second hydrophobic surfactants comprise about 3.5% w/w of the formulation.

4. The topical formulation of claim 1, wherein the blended HLB of the first hydrophilic and second hydrophobic surfactants is 13.6.

5. A stable topical formulation comprising:
(i) 1.05 (% w/w) pexiganan acetate
(ii) 20.0 (% w/w) propylene glycol
(iii) 0.1 (% w/w) EDTA
(iv) 7.5 (% w/w) stearyl alcohol
(v) 2.0 (% w/w) cetyl alcohol
(vi) 1.0 (% w/w) isopropyl myristate
(vii) 0.1 (% w/w) BHT
(viii) 0.43 (% w/w) Span 60
(ix) 3.07 (% w/w) Tween 60
(x) 0.1 (% w/w) Tween 80 and
(xi) (q.s.a.d.) sodium acetate buffer.

6. A stable topical formulation comprising:
(i) 1.05 (% w/w) pexiganan acetate
(ii) 20.0 (% w/w) propylene glycol
(iii) 0.1 (% w/w) EDTA
(iv) 6.0 (% w/w) stearyl alcohol
(v) 2.0 (% w/w) cetyl alcohol
(vi) 3.0 (% w/w) isopropyl myristate
(vii) 0.1 (% w/w) BHT
(viii) 0.17 (% w/w) Span 60
(ix) 3.33 (% w/w) Tween 60
(x) 0.1 (% w/w) Tween 80 and
(xi) (q.s.a.d.) sodium acetate buffer.

7. A method of treating a skin or wound infection comprising topically applying to a patient in need thereof at the site of infection an effective amount of a topical formulation of claim 1.

* * * * *